United States Patent [19]

Dinan et al.

[11] Patent Number: 5,233,049
[45] Date of Patent: Aug. 3, 1993

[54] HIGHLY FLUORINATED BIS-IMIDES

[75] Inventors: Frank J. Dinan, Tonawanda; Willis T. Schwartz, Grand Island; Roger A. Wolfe, Tonawanda, all of N.Y.

[73] Assignee: Occidental Chemical Corporation, Niagara Falls, N.Y.

[21] Appl. No.: 929,602

[22] Filed: Nov. 2, 1992

Related U.S. Application Data

[63] Continuation of Ser. No. 784,287, Oct. 29, 1991, abandoned.

[51] Int. Cl.$^5$ .......................................... C07D 403/10
[52] U.S. Cl. ................................................... 548/462
[58] Field of Search ................................ 548/461, 462

[56] References Cited

U.S. PATENT DOCUMENTS

| | | | |
|---|---|---|---|
| 4,413,131 | 11/1983 | Karanatsios | 548/461 |
| 4,615,832 | 10/1986 | Kress et al. | 252/609 |
| 4,644,066 | 2/1987 | Sonnenberg | 548/462 |
| 4,769,493 | 9/1988 | Ito et al. | 562/480 |
| 4,895,792 | 1/1990 | Stoakley et al. | 528/353 |
| 4,914,212 | 4/1990 | Khuddus | 548/461 |
| 5,076,970 | 12/1991 | Roos et al. | 252/609 |

FOREIGN PATENT DOCUMENTS 263152 11/1987 Japan.

*Primary Examiner*—Joseph Paul Brust
*Assistant Examiner*—Jacqueline Haley
*Attorney, Agent, or Firm*—Wayne A. Jones; Arthur S. Cookfair; Richard D. Fuerle

[57] ABSTRACT

This invention relates to novel fluorinated bis-imides of the formula

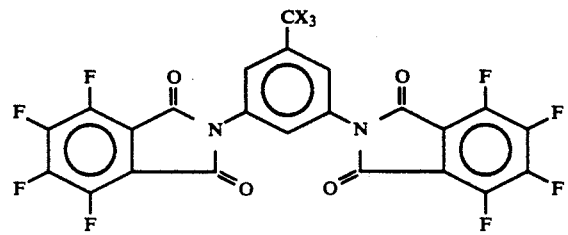

where X is H or F. The compounds are useful as additives to enhance the properties of high performance polymers such as polyimides.

1 Claim, No Drawings

HIGHLY FLUORINATED BIS-IMIDES

This is a continuation of application Ser. No. 07/784,287, filed Oct. 29, 1991 now abandoned.

BACKGROUND OF THE INVENTION

The present invention relates to novel fluorine containing bis-imide compounds useful as additives to enhance the properties of high performance polymers such as polyimides.

Polyimide resins are used in a wide variety of industrial applications, based on their excellent thermooxidative stability, chemical stability, and dimensional stability of molded articles prepared from them. Fluorine-containing polyimides have been found particularly useful for applications requiring low moisture adsorption and high thermal stability.

It is known that the flammability of various material, especially polymeric materials, may be reduced by the incorporation therein of halogen-containing compounds. Various halogenated organic compounds have been useful as fire retardant additives for one type of resin but unsuitable for others because of incompatibility with a particular resin, or inability to withstand particular processing conditions, such as high temperatures. The fluorinated bis-imides of the present invention are particularly useful as additives to polyimide resins to serve as plasticizers and to enhance the already excellent fire retardant properties of such resins.

The incorporation of fluorine containing imide additives into polyimides to enhance the electrical properties, especially to lower the dielectric constant, is shown in U.S. Pat. No. 4,895,972. The patent teaches the incorporation of diamic acid additives, including fluorine containing diamic acids into polyamic acid resins prior to imidization.

U.S. Pat. No. 4,625,832 discloses the incorporation of fluorine containing phthalimides in combination with alkali metal salts, into thermoplastic, branched, aromatic polycarbonates to impart flameproofing properties thereto.

SUMMARY OF THE INVENTION

This invention provides novel fluorine-containing bis-imide compounds of the formula

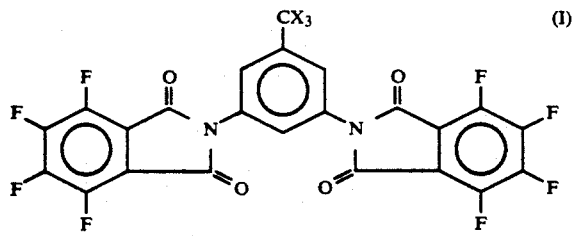

where X is H or F.

The fluorinated bis-imides of this invention are useful as flame retardant additives for various polymeric materials, especially polyimides and polycarbonates. For such purposes, the bis-imide additives are typically incorporated into the polymer in amounts of about 1.0 to about 30 percent by weight, based on the weight of the polymer. Polyimides are generally known to exhibit desirable fire-resistant properties. However, for applications where it is desired to further enhance the already excellent fire-resistant properties, the fluorinated bis-imides of the present invention may be incorporated in the polyimide resins.

The fluorinated bis-imides of this invention may also be employed, optionally, in combination with an alkali metal salt, such as tripotassium or trisodium hexafluoroaluminate, to impart flame proofing characteristics to polycarbonates. The bis-imide compounds of this invention may also be used as plasticizers with various polymers, especially polyimides.

Bis-imides of the present invention as shown in Formula I above, wherein X is hydrogen, are prepared by the reaction of one mold of 3,5-diaminotoluene with two moles of tetrafluorophthalic anhydride. The bis-imides wherein X is fluorine, are prepared by the reaction of two moles of tetrafluorophthalic anhydride with one mole of 3,5-diaminobenzotrifluoride of the formula

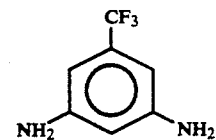

The reaction may be conveniently carried out by mixing the reactants in a solvent such as glacial acetic acid and heating to reflux for a period of time sufficient to complete the reaction, typically, three to four hours. Alternatively, the reaction may be carried out in a polar aprotic solvent at a lower temperature, such as about 15°-30° C., to form the corresponding bis-amic acid which may then be employed as an additive to polyamic acid solutions prior to imidization.

The following examples are provided to further illustrate the present invention and the procedure by which the bis-imides of this invention may be prepared.

EXAMPLE I

A mixture of diaminobenzotrifluoride (1.0 g; 0.0057 mole) and tetrafluorophthalic anhydride (3.6 g; 0.0167 mole) in 30 mL of glacial acetic acid was heated to reflux and maintained thereat for about 3 hours. The reaction mixture was then cooled to room temperature, filtered, and teh solids washed with acetic acid, then hexane and vacuum dried at 100° C. to yield 2.8 g (85%) of the bis-imide of diaminobenzotrifluoride and tetrafluorophthalic anhydride (m.p. 331°-332° C.). The structure and purity (99.4%) was confirmed by GC/MS.

EXAMPLE II

A mixture of diaminotoluene (0.75 g; 0.0061 mole) and tetrafluorophthalic anhydride (4.10 g; 0.0186 mole) in 30 mL of glacial acetic acid was heated to reflux and maintained thereat for about 3.5 hours. The reaction mixture was then cooled to room temperature, filtered, and the solids washed with acetic acid, then hexane and vacuum dried at 100° C. to yield 2.52 g (77.9%) of the bis-imide of diaminobenzotrifluoride and tetrafluorophthalic anhydride (m.p. 310°–311° C.). The structure and purity (98.8%) was confirmed by GC/MS.

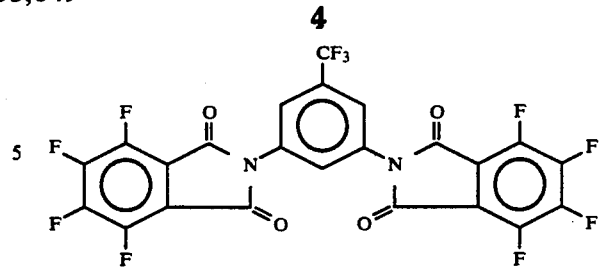

What is claimed is:
1. A bis-imide of the formula